US012682998B2

(12) United States Patent
Gamiello et al.

(10) Patent No.: US 12,682,998 B2
(45) Date of Patent: Jul. 14, 2026

(54) HEALTH PASS SYSTEMS AND METHODS

(71) Applicant: MASTERCARD INTERNATIONAL INCORPORATED, Purchase, NY (US)

(72) Inventors: Dennis A. Gamiello, Yorktown Heights, NY (US); Jonathan Grossar, Jersey City, NJ (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 0 days.

(21) Appl. No.: 17/285,315

(22) PCT Filed: Apr. 13, 2021

(86) PCT No.: PCT/US2021/027050
§ 371 (c)(1),
(2) Date: Apr. 14, 2021

(87) PCT Pub. No.: WO2021/211557
PCT Pub. Date: Oct. 21, 2021

(65) Prior Publication Data
US 2023/0352130 A1      Nov. 2, 2023

Related U.S. Application Data

(60) Provisional application No. 63/057,145, filed on Jul. 27, 2020, provisional application No. 63/019,490, (Continued)

(51) Int. Cl.
*G16H 10/65*          (2018.01)
*G06F 21/60*          (2013.01)
(Continued)

(52) U.S. Cl.
CPC ........... *G16H 10/65* (2018.01); *G06F 21/602* (2013.01); *G06F 21/64* (2013.01); *G16H 40/20* (2018.01); *G06Q 50/265* (2013.01)

(58) Field of Classification Search
CPC ...... G16H 10/65; G16H 40/20; G06F 21/602; G06F 21/64
See application file for complete search history.

(56) References Cited

U.S. PATENT DOCUMENTS

2008/0255944 A1* 10/2008 Shah .................. G06Q 30/0277
                                                                                              705/14.47
2011/0115602 A1    5/2011 Bhandari et al.
(Continued)

FOREIGN PATENT DOCUMENTS

WO          2011005224 A1      1/2011

OTHER PUBLICATIONS

Article by Kovacs, Roxane et al., titled "Can patients improve the quality of care they receive? Experimental evidence from Senegal" published in World Development, 150, 105740, Feb. 1, 2022 (Year: 2022).*

(Continued)

*Primary Examiner* — Raquel Alvarez
(74) *Attorney, Agent, or Firm* — Buckley, Maschoff & Talwalkar LLC

(57) ABSTRACT

System and methods are provided for issuing, using and maintaining passes which may be used to show a current status of approved individuals. In some embodiments, the passes are health passes and the status is a health status.

12 Claims, 8 Drawing Sheets

Related U.S. Application Data filed on May 4, 2020, provisional application No. 63/009,799, filed on Apr. 14, 2020.

(51) Int. Cl.
| | |
|---|---|
| *G06F 21/64* | (2013.01) |
| *G16H 40/20* | (2018.01) |
| *G06Q 50/26* | (2012.01) |

(56) References Cited

U.S. PATENT DOCUMENTS

| | | | |
|---|---|---|---|
| 2015/0234985 A1* | 8/2015 | Saunders ........... | G06Q 20/3278 705/3 |
| 2017/0243463 A1* | 8/2017 | Rdzak .................... | A61J 7/049 |
| 2020/0279631 A1 | 9/2020 | Bass et al. | |

OTHER PUBLICATIONS

International Search Report and Written Opinion date Jul. 12, 2021 which was issued in a counterpart application PCT/SG2010/000261.

* cited by examiner

HEALTH PASS SYSTEMS AND METHODS

CROSS REFERENCE TO RELATED APPLICATIONS

This application claims benefit of and priority to U.S. Provisional Patent Application Ser. Nos. 63/009,799, 63/019,490 and 63/057,145 filed on Apr. 14, 2020, May 4, 2020, and Jul. 27, 2020 respectively, the contents of each of which are hereby incorporated by reference in their entirety for all purposes.

BACKGROUND

As the world becomes increasingly interconnected, it has become more common that businesses, governments, or other entities need a consistent and repeatable way to verify the status or eligibility of individuals. For example, as the COVID-19 virus rapidly spread across the world in 2020 and 2021, and as individuals became vaccinated or had tests results indicating they did not currently have the virus, there was no standard way for businesses, governments or other entities to validate the health status of those individuals.

Identifying an individual's health status (such as whether an individual currently has COVID-19, currently does not have COVID-19 or is currently immune to COVID-19) and granting them appropriate access to social and economic activities would be a powerful way to help re-start economies and begin to reduce the need for social distancing and quarantining.

It would be desirable to provide systems and methods for issuing a pass such as a health pass that may be used to confirm an individual's health status. It would further be desirable to provide such systems and methods in an internationally operable manner. It would further be desirable to provide such systems and methods to confirm eligibility or other status information about an individual.

SUMMARY OF THE INVENTION

According to some embodiments, systems, methods, apparatus, computer program code and means are provided for issuing, maintaining and using health passes that may be used to show a current health status of approved individuals. In some embodiments, a health pass may be issued by receiving a request to issue a health pass to an individual, the request including information identifying the individual and information identifying a health status of the individual, generating an account number and associating the health status information with the account number, and issuing the health pass to the individual for use presenting the health pass at point of interactions to verify the health status of the individual. in In some embodiments, the request further includes information identifying a form factor preference of the individual, the form factor preference identifying at least a first device type to personalize with the account number. In some embodiments, the form factor preference is at least one of a mobile phone, a wearable device, and a physical chip card. In some embodiments, a device may be personalized by causing the account number, a health pass expiry date and cryptographic data to be stored in an application on the device and by enabling the application to access the health status information.

In some embodiments, after issuing the account number, an update request may be received to modify the health status of the individual and the information identifying the health status of the individual may be modified to reflect the updated status.

In some embodiments, a health pass may be used at point of interaction devices. In some embodiments, a point of interaction may transmit a request to identify the health status of an individual. The health pass of the individual identifies an account number which is associated with a health status of the individual. A cryptogram is generated for every request from a point of interaction to verify a health status. The cryptogram may be validated to ensure the health pass is legitimate, and information associated with the health status and retrieved using the account number can be returned to the point of interaction device for display and, in some embodiments, to grant access. a.

Some technical effects of some embodiments of the invention are improved and computerized ways to securely issue, validate, update and maintain health passes for use by a large number of distributed individuals. With these and other advantages and features that will become hereinafter apparent, a more complete understanding of the nature of the invention can be obtained by referring to the following detailed description and to the drawings appended hereto.

DETAILED DESCRIPTION

Figure 1:
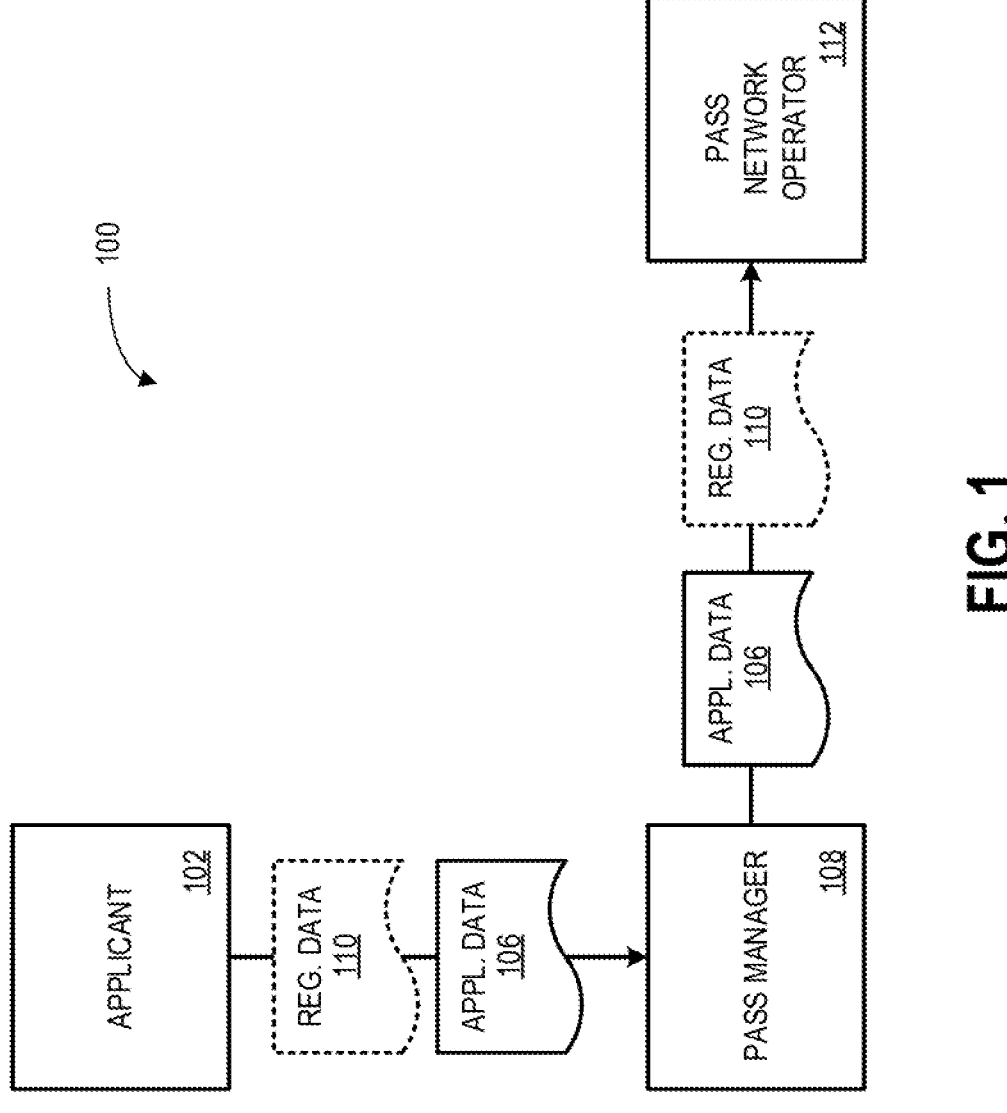
FIG. 1 is a high-level block diagram of a registration processing system according to some embodiments.

The present invention provides significant technical improvements to interactions requiring the verification of information associated with a status of an individual. More particularly, some embodiments are described herein for use in conjunction with verifying information about an individual's health status (although those skilled in the art, upon reading the present disclosure, will appreciate that statuses other than health statuses may be verified using features of the present invention). As described herein, embodiments allow an individual's health status to be accessed via digital certificates that represent the health status of an approved individual. Embodiments allow large numbers of such certificates to be issued, updated and used at point of interaction locations. The present invention is directed to more than merely a computer implementation of a routine or conventional activity previously known in the industry as it significantly advances the technical efficiency, access and/or accuracy of interactions between devices by implementing a specific new method and system as defined herein. The present invention is a specific advancement in the area of healthcare and healthcare status validation and provides benefits in security, privacy and the ability to easily validate information associated with an individual's health status at point of interaction locations around the world. Embodiments remove the need to contact a health care provider to validate the health status at a point of interaction device. Even when the validation is performed online, it is performed on a network (such as the Banknet network operated by the assignee of the present application) which processes billions of transactions and is highly reliable (as opposed to approaches that may require an Internet connection to each health care provider which can be less reliable). The present invention provides improvement beyond a mere generic computer implementation as it involves the processing, validation and controlled access to highly sensitive data for a large number of individuals around the world in a new and beneficial manner as well as the interaction of a variety of specialized client and/or third-party systems, networks, and subsystems. For example, in the present invention, information may be processed, managed, and/or used to validate the health status of individuals despite complex testing and regulatory environments.

For convenience and ease of exposition, a number of terms are used herein. For example, the terms "individual", "user", "citizen" or "applicant" are used interchangeably herein to refer to an individual who is applying to be issued a health pass for use pursuant to the present invention. Pursuant to some embodiments, an "individual", "user", "applicant" or "citizen" may be located in any jurisdiction which supports or allows use of the health pass of the present invention. As an illustrative but not limiting example, an individual may be, for example, an employee who wants to get access to work location(s) and whose organization has agreed to participate in the system of the present invention. As another example, an individual may also be a person who wishes to travel and an airport, government or airline has agreed to participate in the system of the present invention. As a further example, an individual may also be a sport or music fan who wants to access a stadium to attend a sports match or music event in a location that is participating in the system of the present invention. As used herein, the terms "registered user", "registered pass holder", "health pass holder" or "verified applicant" are used to refer to an individual, user, citizen or applicant who successfully applied for a health pass and whose application was approved and who has been issued a health pass pursuant to the present invention.

As used herein, the term "health pass" is used to refer to a dynamic digital certificate or other validation issued by a local government or government-trusted third party that indicates that a holder of the pass (the "pass holder") has a certified health status. For example, the health status may be a confirmation that the holder has recently tested negative on an approved antigen test (confirming the individual does not currently have COVID-19), a confirmation that the holder has recently tested positive on an approved antibody test (confirming the individual has had but has recovered from COVID-19), or a current vaccination status (e.g., such as a vaccination for the current year's influenza or a particular vaccination or series of vaccinations for COVID-19). Other certified health statuses may also be represented or validated by the issuance of a health pass pursuant to the present invention as will be further described herein. The term "pass" may also be used herein to refer to a dynamic digital certificate or other validation issued by an entity (such as a government or the like) that indicates a status of the holder of the pass (the "pass holder") for statuses other than health statuses (e.g., such as the age of a holder, student status, resident status, etc.).

As used herein, the terms "pass network operator" or "network operator" are used to refer to an entity that operates a health pass network as described herein. For example, in some embodiments, the network operator is an entity such as MasterCard International Incorporated (the assignee of the present invention) and the health pass network consists of a network operated by MasterCard International Incorporated such as, for example, the BANK-NET® network. Those skilled in the art, upon reading the present disclosure, will appreciate that other networks and network operators may be configured to operate pursuant to the present invention.

As used herein, the terms "pass facilitator" or "approved pass source" (or simply "medical facility" when used in the context of passes that are used as health passes as described herein) are used to refer to entities or systems that have been authorized by regulatory bodies and/or the operator of a pass network to receive applications (such as pass or health pass applications) from applicants and process those applications. In some embodiments, a "pass facilitator" or "approved pass source" may be authorized to issue passes pursuant to some embodiments. As a specific example, a "health pass facilitator" may be a laboratory that performs testing such as COVID-19 testing. When an individual's test results are communicated to the individual, the laboratory may offer the individual the option to apply for a health pursuant to the present invention. In some embodiments, such laboratories may be in a desirable position to act as a health pass facilitator as the laboratory is in possession of the final test results as well as detailed information about the nature of the test conducted. In general, the responsibilities of a medical facility or health pass facilitator may include (i) verifying the identity of the citizen asking to perform testing as part of the inventive system—at time of registration and at time of test, (ii) confirming, through an enrollment application or web portal provided by an operator of the system of the present invention, the identity of the citizen (including the citizen's picture for a health pass), the lab test results (e.g., negative, positive to antibody test or vaccinated) and the date of the test, and (iii) in some embodiments, provide the citizen with a physical contactless card for accessing the health pass.

As used herein, the terms "health pass network partners", "pass network partners" or simply "network partners" are used to refer to entities that participate in the pass network of the present invention such as, for example, entities that provision devices for use as health passes. As an illustrative but not limiting example, an entity such as a manufacturer of wearable fitness monitors (such as those provided, for example, by Fitbit, Inc.) may be a health pass network partner by being certified to provision software and information onto a wearable device owned and controlled by a health pass holder.

As used herein, the term "program owner" refers to an entity (such as a corporation, a governmental entity, or the like) that owns or operates the health pass program of the present invention. As used herein, the terms "pass manager" or "health pass manager" may be used to refer to an entity or entities that participate in the pass network of the present invention and which perform issuance servicing and application management (although both functions may be performed by the same entity, they may also be performed by separate entities). The pass manager may act as an issuance service provider to issue (or facilitate the issuance of) digital and/or physical health passes pursuant to the present invention. In some embodiments, the pass manager may perform issuance services to provide, support and maintain a software development kit (or "SDK") which allows third parties to build services that integrate with a health pass application built and distributed by an application manager. For example, an SDK may implement the Mastercard Cloud Based Payments ("MCBP") specifications and may include mechanisms to (i) enable device authentication in the health pass application (e.g., PIN or device biometrics) to protect access to the information stored on the health pass and to provide access to the generation of QR codes or other cryptograms (e.g., provided via an NFC interface) which can be used to provide ownership of a valid health pass, (ii) generate (after successful user authentication) a dynamic cryptogram generated from a token and keys provisioned by a service such as the Mastercard Digital Enablement Service ("MDES"), include (in a QR code or via an NFC interface) a dynamic cryptogram, a URL to the citizen's photo (validated during an ID&V process) and, in some embodiments, additional health pass attributes. The health pass manager may also receive provisioning or revocation requests from an orchestration service (as described further below) and to connect to MDES to request from MDES the provisioning of a digital pass or the revocation of a pass. In the case of a physical pass, the pass manager may be responsible for (i) receiving requests from the orchestration service to manufacture and personalize physical contactless cards and (ii) send the personalized cards to the medical facility (or some other participating organization) or to the individual directly.

In some embodiments, the pass manager may also function as (or only function as) an application manager which is responsible for managing the creation and the distribution of the pass application on behalf of a program owner (e.g., such as a corporation or governmental entity). The responsibilities of the application manager include (i) building the pass application and integrating the SDK from an issuing service provider and (ii) distributing the health pass application to citizens. The pass application may include mechanisms to (i) register the user, and capture user consent to use the application under the health pass program run by a program owner—optionally, register dependents (e.g. children) over which the user has legal authority, (ii) capture the citizen's picture (e.g., as a selfie) within the pass application at the time of registration, (iii) setup authentication mechanisms for accessing the application unless it leverages the mechanisms provided by the SDK, and (iv) in some embodiments, create a claim with information provided by citizens on their identity and lab results, and forward the claim securely to an orchestration service for validation.

In some embodiments, an orchestration service is provided to confirm whether a citizen is eligible to receive a health pass and to request the issuance (or revocation) of a health pass. In some embodiments, rather than using an orchestration service (or in addition to), a web portal may be used to confirm the issuance of a health pass to participating citizens.

In some embodiments, the orchestration service may support face-to-face ID&V where a system operator provides medical facilities with an enrollment application which is used by the medical facilities to confirm that they have verified the citizen's identity and confirm test results. The application is connected to the orchestration service and the service receives from the application a confirmation that the citizen's identity was verified and the test results (test type/test date). In some embodiments, the orchestration service may support remote ID&V in which the citizen's health pass application is connected to the orchestration service, which in turn is connected to multiple identity verification services and health record verification services.

These services function to validate citizens' claims on their identity and on the test which they performed. In either embodiment, the orchestration service connects to or is in communication with the health pass manager and issuance service providers (to issue digital or physical health passes) In some embodiments, the issuance service providers may further provision the test results as part of a set of health pass attributes (e.g., such as part of an MDES profile).

A decision management platform may also be provided to share the test results which shall be used during the validation process to enforce relying party requirements (e.g. a certain type of test or requirements on when the date at which the test was performed). This connection is not required if the form factor on which the health pass is stored is able to share the test results directly with the health pass validator at time of validation.

Another type of "health pass network partner" or "network partner" may be entities that perform identity verification services. For example, some network partners may be authorized to perform applicant identification and verification ("ID&V") services. These network partners may also be referred to herein as "identity and verification providers".

Applicants have realized that it would be desirable to provide systems and methods for validating a status of an individual by use of a pass. More particularly, embodiments will be described by referring to embodiments in which the status of the individual is a health status (e.g., such as an immunity status, a vaccination status, etc.). Those skilled in the art will appreciate that embodiments may be used in conjunction with validating other types of statuses as well.

Features of some embodiments of a health pass will be described by reference to the following figures and accompanying text. In general, the following will describe embodiments that allow an individual to register for a health pass (FIG. 1), perform identity and verification and validation (FIG. 2) and to use the health pass to obtain access or otherwise verify the individual's health status (FIGS. 4-7). Further, embodiments will be described which illustrate the provisioning of a health pass in various devices that the individual can then use to present their health status (FIG. 3). Pursuant to some embodiments, the health pass is issued and operated using an international, highly available network that allows the issuance, updating (including revocation) and continuous validation of health passes for large populations of individuals.

FIG. 1 is a high-level block diagram of a registration system 100 according to some embodiments of the present invention. In particular, the registration system 100 includes components that interact to allow an applicant 102 to submit an application with application data 106 and request that a health pass manager 108 optionally provide health pass registration data 110 to a health pass network operator 112 (where the registration data 110 may be used for a remote ID&V process as described further below in conjunction with FIG. 7). Pursuant to some embodiments, the health pass network operator 112 is the operator of an international, highly available processing network. As an example (which will be carried throughout the remainder of this description), the health pass network operator 112 may be Mastercard International Incorporated (referred to herein as "Mastercard") and may be referred to as both the operator of the network as well as the network and components thereof. In some embodiments, some or all of the health pass network may be operated by or on behalf of a government or a governmental entity. While embodiments may be used to issue and validate different types of "passes", embodiments will be described using the specific example of "health passes".

Figure 2:
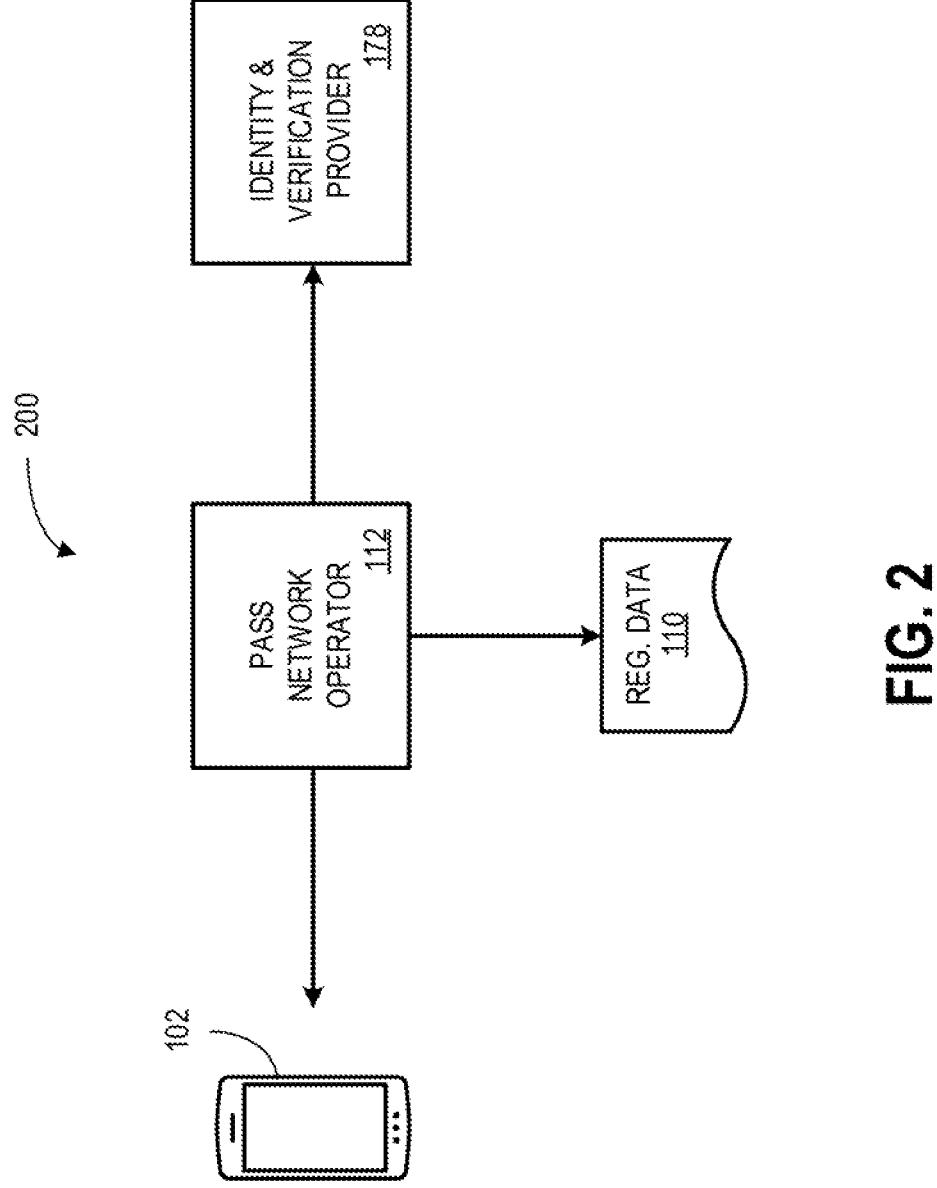
FIG. 2 is a high-level block diagram of an identification and verification processing system according to some embodiments.
Figure 3:
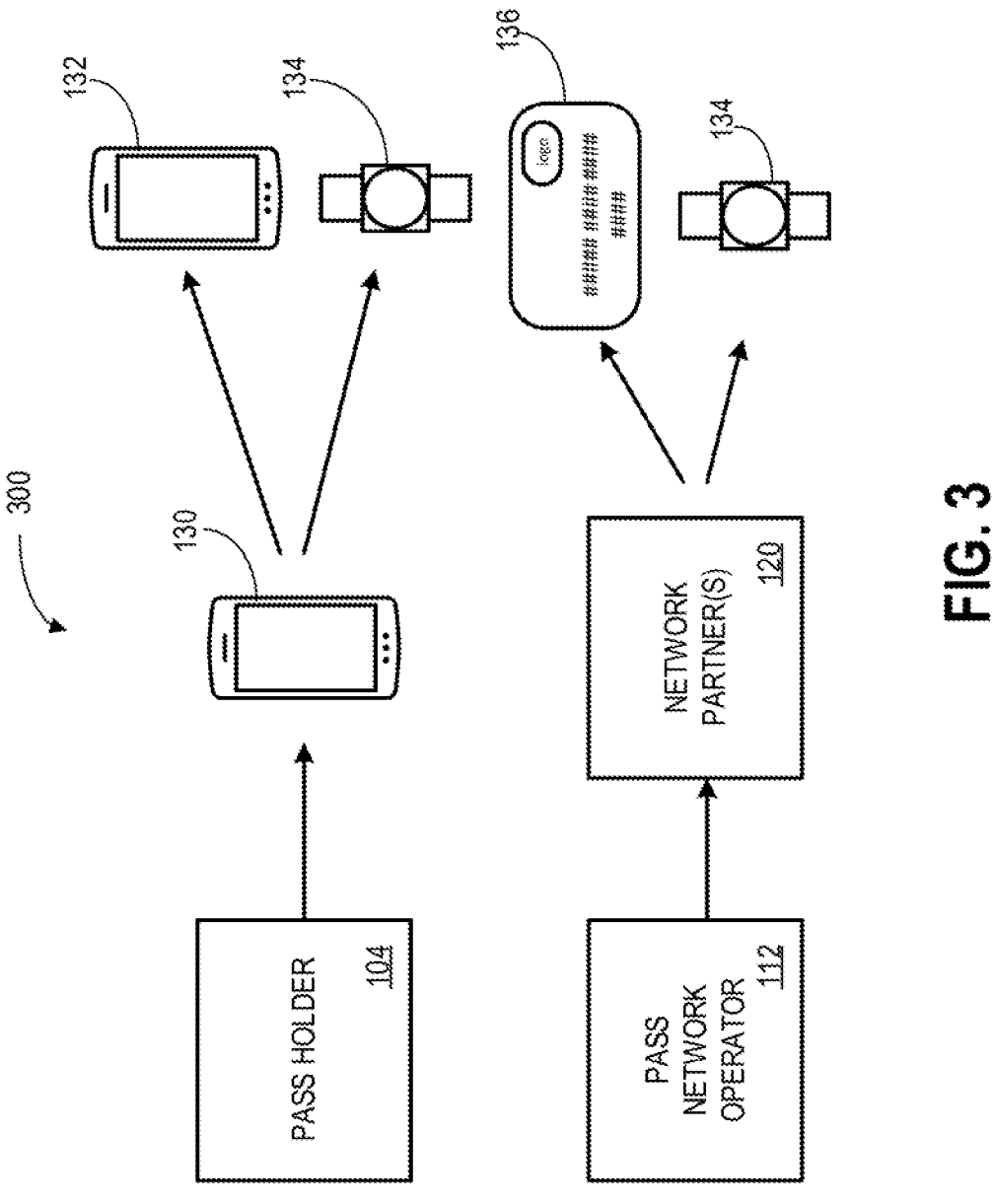
FIG. 3 is a high-level block diagram of a health pass provisioning system according to some embodiments.
Figure 6:
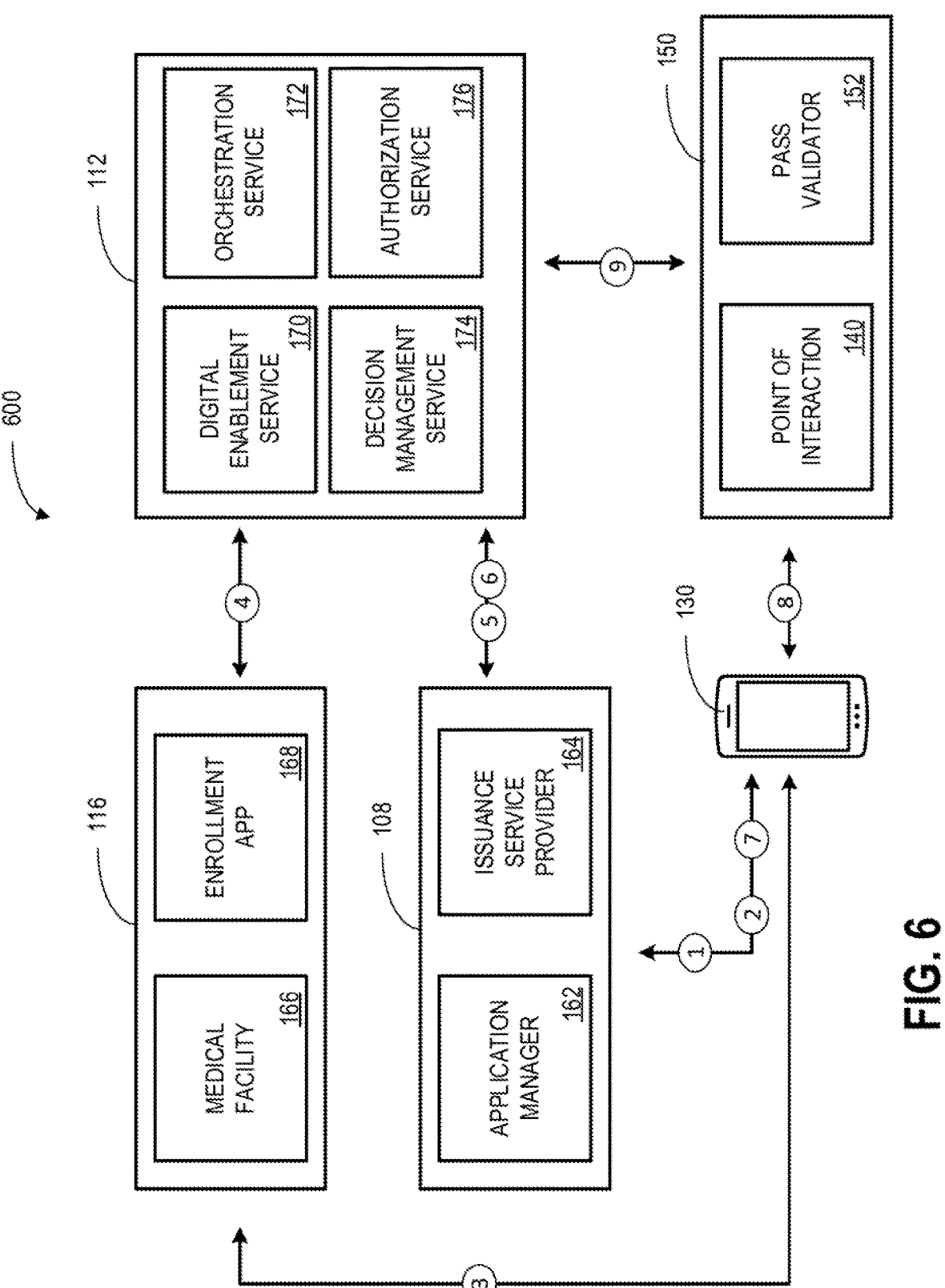
FIG. 6 is a block diagram of an embodiment of a health pass system in which ID&V is performed locally.
Figure 7:
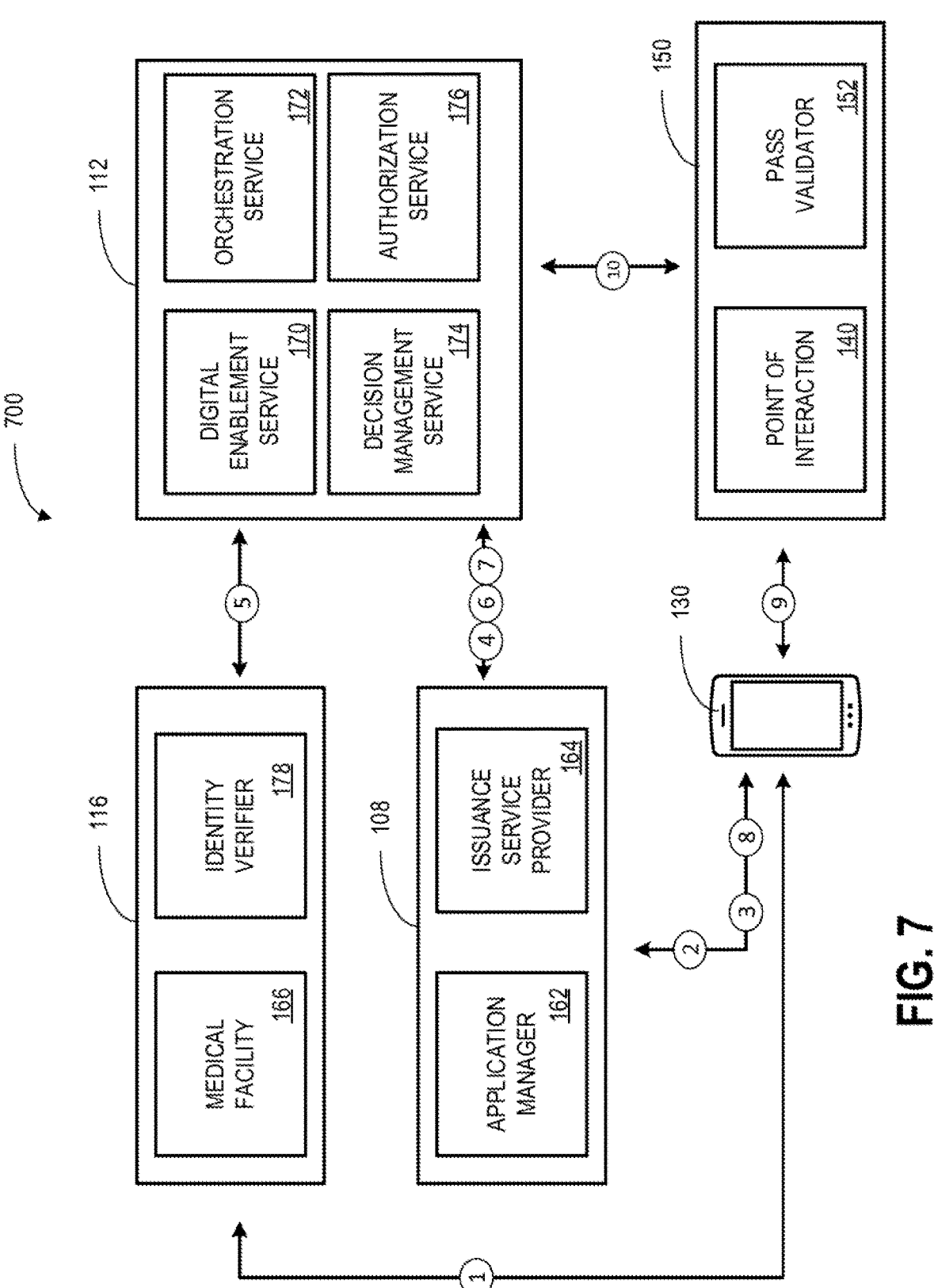
FIG. 7 is a block diagram of an embodiment of a health pass system in which ID&V is performed remotely.

The health pass network operator 112 may be in communication with a plurality of entities or devices, some of which are shown in FIGS. 1 and 2 and some of which will be shown in FIGS. 6 and 7. As shown, the health pass network operator 112 may be in communication with one or more health pass facilitators 116 via one or more secure network connections. Pursuant to some embodiments, each facilitator 116 has been approved to participate in the health pass system of the present invention and is certified to apply a test method agreed to in the health pass program (e.g., each health pass facilitator may be certified by a relevant program owner such as a local governmental entity or the like). For purposes of illustration, the health pass facilitator 116 will generally be described herein as a certified testing provider or laboratory although other types of entities may also function as health pass facilitators 116. In general, pursuant to some embodiments, a health pass facilitator 116 may be responsible for performing testing for which a health pass may be requested (e.g., such as COVID-19 testing or the like). The health pass facilitator 116 may also be responsible for some identity and verification processing which will be described further below in conjunction with FIGS. 6 and 7. Other entities (described further below in FIGS. 6 and 7) may participate in the system of the present invention, including one or more health pass managers 108 which perform functions such as distributing a health pass application from which a health pass may be requested or such as facilitating the issuance of digital and/or physical health passes. Further details of these different functions will be described further below in conjunction with FIGS. 6 and 7.

The health pass manager 108 may receive application data 106 in a request from an applicant 102. The request from the applicant 102 may be a request to apply for a health pass (e.g., in conjunction with obtaining a test result). In response to the request, the health pass manager 108 may collect information from the applicant 102 as well as from information known to the health pass facilitator 116 (for example, the health pass facilitator 116 may have direct access to information associated with testing results to be associated with a health pass). In some embodiments, an application will be declined if the applicant 102 has not taken a diagnostic test (or if the results are not yet available, are inconclusive, or are otherwise unsuited for forming the basis of a health pass). As a specific illustrative example, the health pass manager 108 may be an entity operating a health pass application or web page on behalf of a corporation, a medical facility, a governmental entity or the like, and offers the applicant 102 an opportunity to apply for a health pass before the applicant requests a test from the provider or after the applicant performed a test at the provider.

Pursuant to some embodiments, the interaction between the applicant 102 and the health pass manager 108 may be via a secure Internet connection (e.g., such as via a health pass application or via a secure Web page distributed or hosted by the health pass manager 108 on behalf of health pass facilitators 116, corporations, governmental entities or the like). For example, in some embodiments, the applicant 102 may interact with the health pass manager 108 via a secure Web page to submit a health pass application or to view the applicant's testing results. The Web page may include information prompting the applicant to apply for a health pass pursuant to the present invention. If the applicant 102 chooses to apply, the Web page may prompt the applicant 102 for any further information required to issue the health pass. For example, in some embodiments, the information collected may include information identifying the applicant. In some embodiments, a photo of the applicant may also be collected (such as, for example, a photo associated with a governmental entity such as a driver's license or a passport, although a photo obtained during registration may also be used in some embodiments).

The health pass manager 108 transmits the health pass application data 106 to the health pass network operator 112 and may also transmit the health pass registration data 110 for use in a remote ID&V process (e.g., as described further below in conjunction with FIG. 7). In some embodiments, the health pass registration data 110 includes applicant information such as, for example, the applicant's name, address, mobile phone number, email address, national identifier (e.g., such as a social security number, taxpayer identification or the like). The registration data 110 also includes the test or health related information for which the health pass is to be issued. For example, the registration data 110 may include information identifying the testing provider, the location of the test, the date of the test, the type of test performed, the testing results and any other relevant test information for use in validating the applicant's health status. In general, the registration data is shared with the network operator 112 in an encrypted format. Those skilled in the art will appreciate that any personal or healthcare data stored or transmitted will be done pursuant to the laws of each jurisdiction in which the system of the present invention operates. Different approaches for performing ID&V will be described further below in conjunction with FIGS. 6 and 7.

The registration data 110 may also optionally include a selection or indication of the form factor in which the applicant 102 wishes to access the health pass. For example, as will be described further below, a health pass pursuant to the present invention may be accessed and used in a number of form factors such as, for example, a Wallet application on a mobile device, a physical card, a wearable device (such as, for example, a fitness tracker or smart watch) or the like. The criteria and registration process may vary based on regional requirements and regulations, and not all registration information may be required or available. In any event, the registration data is provided to the health pass network operator 112 via a secure communication channel. In some embodiments, the registration data is stored in an application queue or database and is associated with information identifying the health pass facilitator 116. The information identifying the health pass manager 108 may be used during personalization of devices (as described in FIG. 3, below) and may also be used in the issuance of a health pass as will be described elsewhere herein.

Once the registration data has been received, the health pass network operator 112 performs processing to ensure the identity of the applicant 102 is properly verified. Reference is now made to FIG. 2 where a block diagram depicting the identification and verification ("ID&V") processing system is shown. As depicted, the ID&V process includes participation of several entities, including the applicant 102, the health pass network operator 112 and one or more identity verification providers 178 (all communicating via one or more secure networks or channels). More particularly, the health pass network operator 112, upon receiving registration data 110 associated with an applicant 102, may determine that an ID&V process is required to verify the applicant's identity. Using information provided in the registration data 110 the health pass network operator 112 initiates communication with the applicant 102 using the provided mobile phone number (e.g., via an automated call or SMS message) or email and by sending a one-time activation code. The applicant 102, upon receipt of the activation code, may be required to enter the activation code in a Web page or other interface provided by the health pass manager 108 in order to validate the applicant information.

In some embodiments, additional security measures may be required and the health pass network operator 112 may perform additional processing to verify the registration data 110 and/or to verify the identity of the applicant 102. For example, the health pass network operator 112 may communicate with one or more approved identity verification providers 178 to (i) validate the provided name, address and email, (ii) validate possession and location of the phone, and/or (iii) validate a shared secret such as the national ID or a case number assigned to the application. Such validations may be made using historic reference sources or other sources available to the identity verification providers 178.

Pursuant to some embodiments, a health pass assurance level may be assigned to a given health pass in light of the type of ID&V that was performed in issuing the health pass as well as the entity performing the ID&V. Different ID&V's may result in different health pass assurance levels. An entity that wishes to verify information about a user's health condition may wish to know the level of assurance and the data that was used to generate the level of assurance with a health pass prior to allowing the user access or entry to a location or place of employment. The assurance level that is assigned to a health pass may change over time and be re-calibrated based upon factors that influence the assurance level confidence levels (such as the nature of documentation provided by the user to obtain the ID&V). Further details of different ID&V approaches will be described further below in conjunction with FIGS. 6 and 7.

For ease of exposition to describe features of some embodiments, the above description of FIGS. 1 and 2 generally describes a process in which an applicant requested a health pass via an application or via a Web interface. In some embodiments, an applicant may request a physical health pass when the individual is at a medical facility. Processing of such an embodiment generally follows the processing as described herein (other than the individual's interactions via an application or via a Web interface). Further, in the description of FIGS. 1 and 2, an embodiment is generally described in which registration data is provided to the network operator 112 (e.g., for use in remote ID&V processing). In some embodiments, the registration data may be shared with a health pass facilitator 116 (e.g., in in-person ID&V processing) via a QR code containing the registration data as described further herein. In this embodiment, the registration data 110 is not shared with the health pass network operator 112. In both cases (in-person (ID&V and remote ID&V) testing data is shared with the health pass network operator 112 to be provisioned into the health pass pursuant to the present invention.

Once the identity of the applicant 102 and the registration data 110 have been validated, the health pass network operator 112 may issue a health pass to the applicant 102. In some embodiments, health passes may be issued with expiration dates or periods of validity. In some embodiments, as a holder's health status changes (e.g., as subsequent tests are administered or as information indicating that the health status may have changed such as the collection of contact trace information implicating the holder), the issuer or a governmental entity may revoke or modify the health pass. In some embodiments, the health pass network operator 112 may provide a secure channel to such entities to initiate status changes. The status changes may then be imposed by the health pass network operator 112 directly on the health pass or in information provided during authorization processing.

To allow health passes issued pursuant to the present invention to be accessible around the world at a large number of locations, embodiments utilize existing networks and transaction devices in those networks. For example, in some embodiments, the health pass of the present invention may be operable in conjunction with a payment network such as the BANKNET network referenced above. More particularly, pursuant to some embodiments, a health pass may be operable or accessible using network message formats compatible with payment networks such as, for example, messages that conform to the International Organization for Standardization (ISO) Standard 8583, "Financial transaction card originated messages-Interchange message specifications", ("ISO-8583"). ISO-8583 is a standard for payment system messages and includes messages such as an authorization request message and an authorization response message. Pursuant to some embodiments, a health pass status associated with a health pass holder may be accessed by presenting a device personalized with a health pass (as described below in conjunction with FIG. 3) at a terminal or other device. The terminal or other device causes information associated with the health pass to be transmitted to the health pass network operator 112 in a standard payment message format (such as one compliant with ISO-8583 or the like). The health pass network operator 112, using information from the message, validates the authenticity of the health pass and may determine the health pass status and returns information associated with the status to the terminal or other device for display. The information is returned to the terminal or other device using a standard payment message response format (again, such as one compliant with ISO-8583 or the like).

As a simple illustrative example, an individual (a "health pass holder") who has been vaccinated against COVID-19 may be issued a health pass for use in confirming that status to interested parties (such as, for example, employers, border agents, medical professionals, airlines, or the like). The health pass may be accessible via an electronic wallet of the health pass holder's mobile phone. When the health pass holder wishes to confirm their health status to an interested party, the health pass holder presents their mobile phone to a terminal associated with the interested party (e.g., such as a terminal at a border crossing station or point of entry). Information from the health pass is communicated in a payment system message (e.g., in an ISO-8583 authorization request message) and it is routed to the health pass network operator 112.

Pursuant to some embodiments, the terminal may be configured to identify the type or nature of health pass required by the interested party. For example, the interested party may be a border agent at a border crossing in a jurisdiction that requires testing results from a test that was conducted within the past two weeks. Terminals at that border crossing may be configured to transmit authorization request messages that include such requirements. Other types of requirements may also be specified, such as, for example, the type of test, a test methodology (e.g., to adhere to certain standards), the type of laboratory or testing facilities that are acceptable, or the like.

The health pass network operator 112 validates the authenticity of the health pass and accesses the health status information associated with the health pass and returns that health status information to the terminal associated with the interested party. In some embodiments, a device such as a mobile device having a health pass application thereon (or a health pass enabled wearable device or a physical health pass) may share information associated with the status directly with a point of interaction device. Such embodiments may be used in both online and offline use cases. The status information may simply be an indicator that the health pass holder does not have COVID-19. In some embodiments, the status information may also include further information about the nature of the status (such as, for example, information about the type of test that was performed on the holder, information about the date of the test, or the like). In some embodiments, the terminal inserts information about such requirements into the authorization request and relies on the health pass network operator 112 to apply the requirements to the health pass information before returning a result (e.g., the health pass network operator 112 will determine whether a health pass associated with an individual meets the requirements specified by the terminal). In some embodiments, the terminal may simply request the details be returned by the health pass network operator 112 in an authorization response and the terminal will apply logic to determine whether the health pass associated with the individual meets the requirements.

In order to enhance the security of health pass transactions, as well as the confidence that the health pass holder is an authorized holder and that the health pass network provider is authorized to provide the health status information, some embodiments may use secure transaction methods such as those that are compliant with the EMV interoperable payments specifications set forth by EMVCo, LLC (available at http://www.emvco.com). The remainder of this disclosure will be presented using examples that generally follow the EMV specifications; however, those skilled in the art, upon reading the present disclosure, will appreciate that other standards or schemes may also be used so long as they are secure.

In the context of an EMV-compatible transaction, a set of cryptograms may be utilized to authenticate that the health pass as well as the health pass facilitator (or entity providing the health pass status information) is authentic. Preferably, such cryptograms may be utilized in both online transactions (transactions where an authorization request can be transmitted to the health pass network operator 112 to authenticate the cryptograms) as well as offline transactions (transactions where the health pass must interact with an offline terminal or terminal not currently in communication with the health pass network operator 112 to authenticate the cryptograms). In general, in an online transaction, the health pass device (e.g., such as a mobile phone, a chip card, a wearable device, etc.) generates a cryptogram using a key stored in the device and information about the request and transmits the cryptogram and the request to the health pass network operator 112 (e.g., via an ISO-8583 authorization request message). In EMV terms, this cryptogram is generally referred to as the authorization request cryptogram ("ARQC"). The information associated with the request may include a health pass account number (generally referred to as a "PAN" or primary account number), an expiration date of the PAN, information associated with the terminal, and potentially other information.

The health pass network operator 112 (or the issuer of the health pass), upon receipt of the request message, attempts to recreate the ARQC using information from the request (including the PAN, the expiration date, or the like) as well as its version of the key. If the cryptogram generated by the health pass network operator 112 matches the received ARQC, the network 112 can authorize the health pass request (as it has confirmed that the request came from a legitimate health pass) and provide a response to the request. Creation of the response may include retrieving the health status information from a secure database using the PAN as a look up identifier. The health status information may be returned to the health pass/terminal in a response message (such as one formatted in accordance with ISO-8583). The response message may include the status information, any expiry or other meta attributes associated with the status.

The terminal (if present), upon receiving the response message, may first confirm that the response code from the network 112 is valid (to authenticate that the network 112 was legitimate) and then process the status response to display the status information. In this manner, embodiments allow for a secure health pass processing environment in which the authenticity of the participating components can be authenticated using cryptographic techniques. Further, transactions may be processed using existing components and infrastructure. In some embodiments, health pass holders may be authenticated or verified by requiring that the holder perform some validation method (such as entering a PIN or performing some other action).

In some embodiments, the PAN that is used to identify a health status record may be a tokenized PAN such as one issued pursuant to the EMV Tokenization standards. In some embodiments, each device that is provisioned with a health pass PAN may be provisioned with a tokenized PAN enabling an individual to have several devices each identified by a unique tokenized PAN.

Reference is now made to FIG. 3 where several device provisioning options are shown which allow a PAN and associated cryptographic data to be stored in a secure application of a device that a health pass holder wishes to use for storage and use of their health pass. As described above, in some embodiments, health passes are configured to comply with the EMV standards. As such, the personalization of devices may also comply with the EMV standards.

In some embodiments, a health pass holder may wish to use and access the health pass as a digital pass. In the case of a digital pass, the health pass may be provisioned on or in a Wallet on a mobile device 132, in a dedicated health application on a mobile device 132, or on a wearable 134 (such as a fitness band, a smart watch, etc.). In such embodiments, the provisioning may be initiated from an existing Wallet or application on a mobile device such as mobile device 130. In some embodiments, a health pass network operator 112 may interact with one or more network partners 120 to provision, activate and distribute physical devices such as chip or magnetic stripe cards 136 (e.g., such as in a credit card sized form factor or the like) or wearables 134. Once a holder has been issued a health pass and one or more devices associated with the holder have been personalized as described herein, the holder can use the health pass in a number of different environments as will be described further below in conjunction with FIGS. 4-6.

Pursuant to some embodiments, each device provisioned to utilize the health pass may be provisioned using a service such as the Mastercard Digital Enablement Service ("MDES") which is operated by the assignee of the present application. For example, in some embodiments, the health pass holder devices shown in FIG. 3 may be provisioned using a push provisioning service with the MDES Token Connect service (e.g., to push an existing payment card into the health pass program, such as, for example, a non-transactable tokenized version of an existing payment card). In such embodiments, the devices are provisioned to access the health pass associated with a health pass holder using a tokenized PAN that is unique to each device and that may be used by the health pass network operator 112 to perform health pass authorization processing as described herein.

Figure 4:
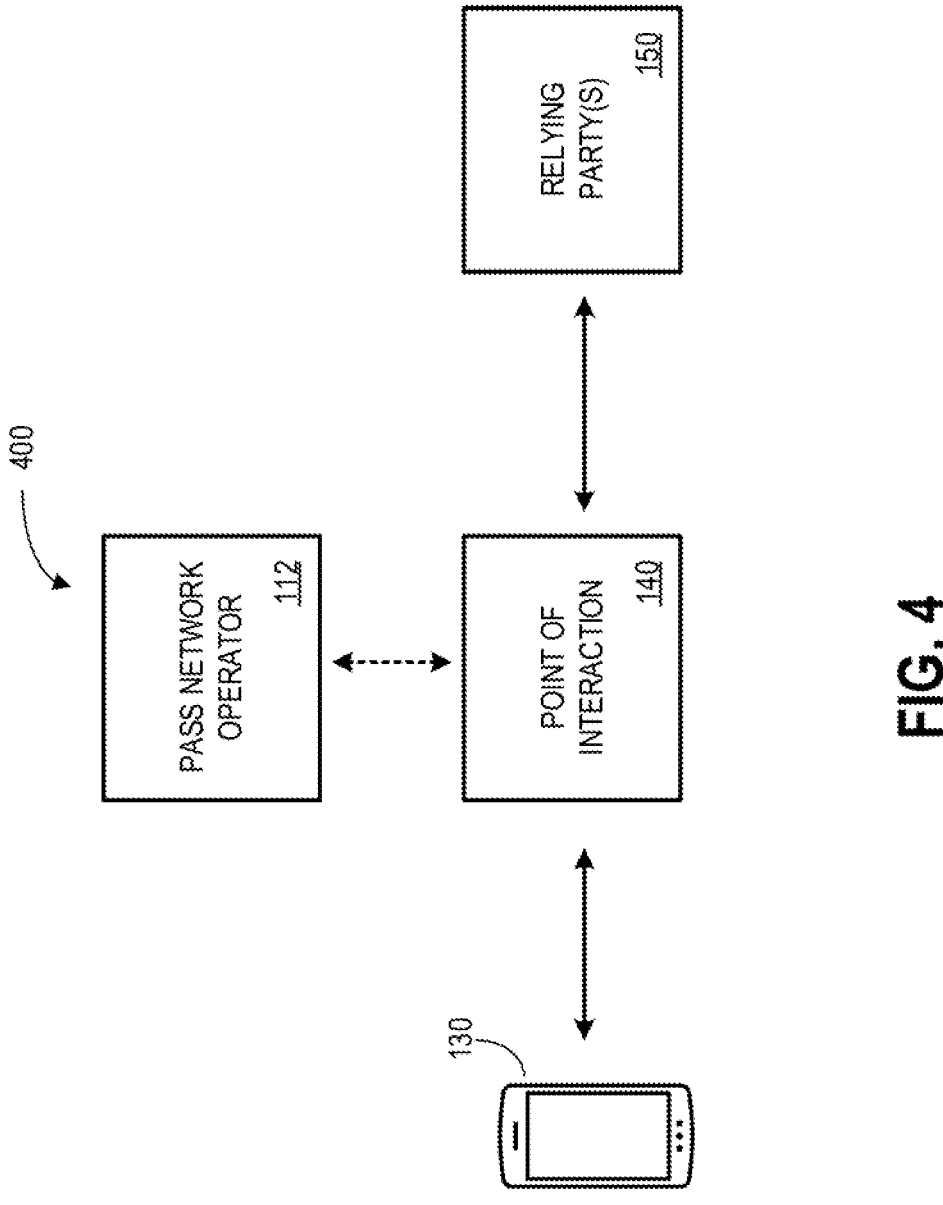
FIGS. 4-5 are high-level block diagrams of health pass transaction systems according to some embodiments.

In some embodiments, such as shown in FIG. 4, a health pass holder may need to present their health pass to prove their health status in in-person environments. For example, a health pass holder having, for example, a mobile device 130 provisioned with a PAN that allows access to the health pass may need to prove their status to gain access to a sensitive or controlled environment (such as, for example, a place of employment). In such an environment, a transaction may proceed as follows. First, the health pass holder may operate their mobile device 130 to open or enable the Wallet or health care application (which may, in some embodiments, require an authentication method such as a PIN or biometric to authenticate the holder), and then tap or otherwise present the mobile device 130 to a point of interaction 140. The point of interaction 140 may be a contactless payment device (such as a point of sale terminal) or a device configured to operate as a EMV compatible terminal (e.g., such as a contactless terminal or an EMV enabled point of interaction that is capable of reading QR codes). In some embodiments, the point of interaction 140 may be a mobile device configured to operate as a contactless terminal. In an embodiment where the point of interaction 140 supports online transactions, the processing involves the point of interaction 140 interacting with the mobile device 130 to generate an authorization request message (including any cryptograms as described above) which includes the PAN (or tokenized PAN representing the health pass) and any terminal information (including any health pass requirements, such as a date of validity of a health pass, etc.). The point of interaction 140 then routes the authorization request message to the health pass network operator 112 for processing. The health pass network operator 112 attempts to validate the health pass by performing the cryptogram processing described above. If the health pass can be validated, the health pass network operator 112 may perform additional processing before returning the health status information. For example, the network operator 112 may compare the PAN (or tokenized PAN) to a list of lost or stolen PANs or to an active account list. Further, the PAN (or tokenized PAN) as well as other information from the mobile device 130 may be compared to fraud management and processing rules to ensure the health status is only returned in appropriate circumstances. In offline transactions and online transactions (where the authenticity of the pass is validated by the network 112), the status does not need to be validated by the network 112—instead, the status can be verified in an interaction between the user device and the terminal when the status information is stored in a profile of the user device. The point of interaction 140 may then display information associated with the health status on a display screen or otherwise permit or deny access based on the health status. The point of interaction 140 may also display the picture of the health pass holder which is retrieved from the health pass (if a URL is personalized into the health pass, then it may be retrieved from that URL).

In some embodiments, the point of interaction 140 is not configured to support an online validation. In such embodiments, the point of interaction 140 may be configured to perform offline processing, and, if so, processing involves the point of interaction 140 performing cryptographic processing to validate the cryptogram from the mobile device 130 and may further compare the PAN (or tokenized PAN) with a local blacklist of revoked cryptograms or PANs. Once validated, the health status may be retrieved from the mobile device 130 and the health status may be displayed or used to permit or deny access. While a mobile device 130 is shown in FIG. 4, the device presented may also be a chip card or a wearable personalized with the health pass data as described herein.

In some embodiments, a health pass holder may need to present their health pass to prove their health status in an in-person environment that does not have a contactless point of interaction (as shown in FIG. 4). In some embodiments, the mobile device 130 may be configured to generate a QR code on the mobile device 130 for presentation to a point of interaction 140 (e.g., such as a point of sale reader device). The transaction flow generally follows that of FIG. 4 except that the interaction is via a QR code rather than a contactless communication.

Figure 5:
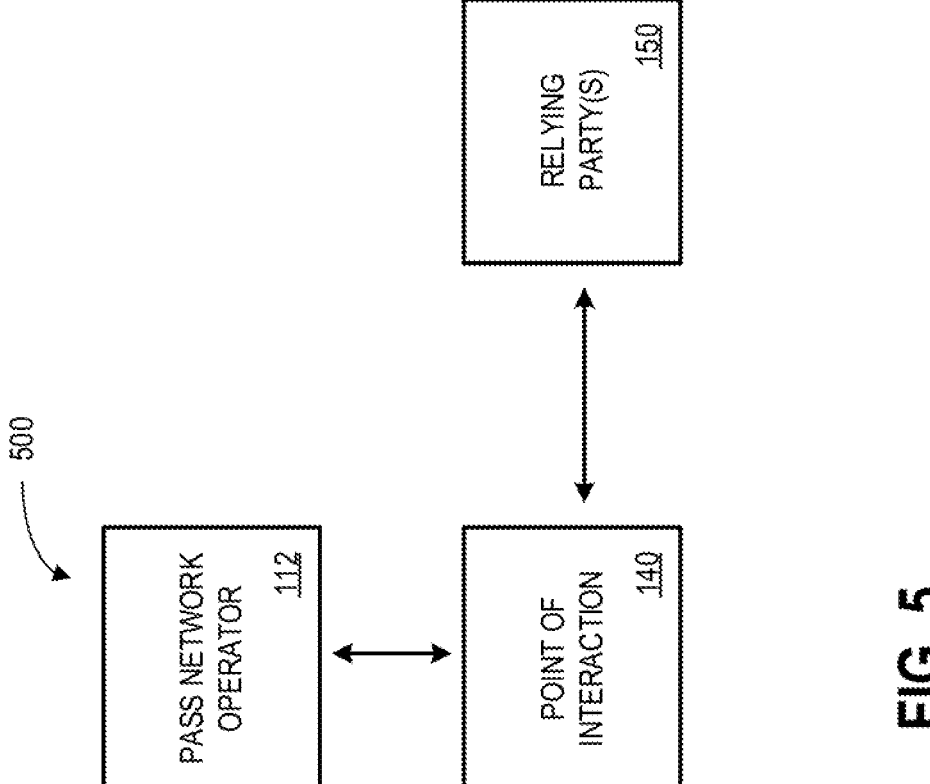

Referring now to FIG. 5, in some embodiments, a health pass holder may need to present their health pass over a remote channel. In such embodiments, the health pass holder may present their PAN (or tokenized PAN) as well as an expiration date and, in some embodiments, a security code. In some embodiments, the PAN may be a dedicated health pass PAN that needs to be input on a Web page associated with a relying party 150. For example, in an illustrative example where the relying party is an airline, the health pass holder may be prompted to enter information (such as the health pass PAN) into a Web page to provide health status information to determine eligibility to travel and to separately provide a payment card PAN to purchase airline tickets. In some embodiments, the PAN associated with a health pass may be a tokenized PAN that is linked to or associated with a payment PAN and the tokenized PAN may be used to both conduct the payment transaction and to verify eligibility or health status. The authorization processing may be performed without the cryptograms described above, however, other validation methods may be used to improve transaction security and validity. For example, device biometric or other biometrics may be used to verify the health pass holder, lost and stolen and other fraud lists may be consulted and other fraud and security processing rules may be imposed.

Pursuant to some embodiments, different verification approaches may be used. For example, in some embodiments, a "face-to-face" verification approach may be used (as described in FIG. 6), and in other embodiments, a remote verification approach may be used (as described in FIG. 7). In some embodiments, both verification approaches may be used in a system pursuant to the present invention.

Referring now to FIG. 6, a system 600 may be provided which supports a face-to-face verification approach. A typical transaction will be described by referring to the numbered messages (labeled "1" through "9" on FIG. 6). First, however, a brief description of each of the components shown in FIG. 6 will be provided, as FIG. 6 provides further details of the applications or configuration of certain elements. For example, as shown, a health pass manager 108 includes several components including an application manager 162 and an issuance service provider 164. The issuance service provider 164 may be a component or an entity associated with a health pass manager 108 and may be configured to issue digital and/or physical health passes pursuant to the present invention. In the case of a digital health pass, the issuance service provider 164 may provide application software to users that are configured to allow devices operated by users to perform health pass issuance processing. For example, an issuance service provider 164 may build and distribute health pass software development kits ("SDKs") for different devices (such as Android or iOS mobile devices) to enable those devices to enable device authentication in a health pass application (e.g., such as PIN or biometrics) to protect access to the information stored on the health pass application and to generate a QR code or a contactless ARQC (for use at a health pass validator 152 to prove ownership of a valid health pass). Further, the SDKs may enable those devices to generate (after successful user authentication) (i) a token and a dynamic cryptogram (ARQC) computed using keys provisioned by the Mastercard Digital Enablement Service ("MDES"), (ii) a photo or a URL to the health pass holder's photo (which is validated during an ID&V process as will be described further herein), and (iii) any health pass attributes (such as test data) retrieved from the health pass profile metadata provisioned by MDES. All the above data can be shared with the point of interaction device over NFC interface or embedded into a QR code that can be read by the point of interaction device. The issuance service provider 164 is also configured to receive provisioning or revocation requests from the orchestration service 172 of the pass network operator 112 and to connect to the digital enablement service 170 of the pass network operator 112 to request the provisioning or revocation of a digital health pass.

In the case of a physical health pass, the issuance service provider 164 may be configured to receive requests from the orchestration service 172 to manufacture and personalize physical contactless cards (e.g., based on a standard such as the M/Chip Advance standard promulgated by Mastercard International Incorporated). In some embodiments, the requests from the orchestration service 172 may include information such as a photo or URL to a photo of the pass holder as well as other health pass attributes (e.g., such as test data or the like). The issuance service provider 164 may also be configured to cause the personalized cards to be conveyed or shipped to a medical facility 166 or to other recipients (including the health pass holder) for distribution.

Pursuant to some embodiments, the application manager 162 may be a component or entity managing the creation and distribution of the health pass end-use application. The application manager 162 is responsible for building the health pass application and integrating SDKs from one or more issuance service providers 164 as well as distributing the health pass application to end users and then supporting those end users in the use of the health pass application. In some embodiments, the health pass application includes controls and features to provide privacy information to the user and capture his or her consent to use the health pass application in the health pass system of the present invention. The health pass application may also include application features that allow the application to register the individual (and, optionally, dependents) and to capture the individual's picture (e.g., as a "selfie") within the health pass application at the time of registration. The picture either resides on the device only (if the intent is to show the picture to a relying party 150) or is exported (and, in some embodiments, encrypted with a device key associated with device 130) to the health pass program owner (for later use in presentation to a relying party 150). The health pass application may also include features that allow authentication mechanisms to be applied to govern how the application and/or its content is accessed. If a remote verification is in the scope of the program (as shown in FIG. 7), the application may also include features to create a claim with information entered by the health pass holder on their identity and lab results and forward the claim to the orchestration service 172 (which connects the relevant identity verifiers and health record verifiers for validation of the claim as will be discussed further below in conjunction with FIG. 7). In some embodiments, the application may allow individuals to modify or revoke their data (note that modification of identity information requires a new ID&V).

Pursuant to some embodiments, the pass network operator 112 may operate one or more applications or components including an orchestration service 172 which is a service that confirms whether an individual is eligible to receive a pass (such as a health pass) and requests the issuance and/or activation and/or revocation of a pass. The orchestration service 172 may operate differently depending on what type of verification mechanism is in scope (e.g., either the face-to-face mechanism of FIG. 6 or the remote mechanism of FIG. 7). If the former, the pass network operator 112 provides the manager 108 with an enrollment application 168, and the manager 108 distributes it to medical facilities 166. The enrollment application 168 may be, for example, installed on a mobile device (such as a laptop, mobile phone, tablet computer or the like) and is used by medical facilities 166 to confirm that they have verified the citizen's identity and to confirm test results. The enrollment application 168 is connected to the orchestration service 172, which receives the following from the enrollment application 168: (1) a confirmation that the citizen's identity was verified and (2) the test results (test type/test date) in an encrypted format.

Referring briefly to FIG. 7, if the verification mechanism used is remote verification, the individual's health pass application (on device 130) is connected to the orchestration service 172, which in turn is connected to one or more identity verifiers 178 (for validating the identity of individuals) and health record verifiers (shown as medical facilities 166 for validating the test results of individuals). Those identity verifiers 178 and medical facilities 166 are validating individual's claims on their identity and on the test which they performed. In both options, the orchestration service 172 connects to the health pass manager 108 (at either the issuance service provider 164 or the application manager 162 depending on the program scope), to initiate the provisioning of a digital health pass and of the test results on the health pass application. The orchestration service 172 connects to the issuance service provider 164 for the issuance of a physical health pass. In some embodiments, the orchestration service 172 also connects to a decision management service 174 to activate a physical health pass, by providing the card identifiers (FPANs).

The pass network operator 112 also includes one or more components or services to perform digital enablement services 170 and decision management services 174. These services are used to deliver a secure and interoperable health pass and to validate health passes when they are presented to a relying party 150 at a validator 152. For example, the services may include functions to: (i) issue card ranges for physical cards on non-transactable BIN ranges; (ii) issue separate tokens and funding account ranges for tokens, on non-transactable BIN ranges; (iii) issue a digital health pass in the form of a token (such as an "MDES" token described herein) and cryptographic keys; (iv) provision the test results in the profile of the token provisioned into the health pass application; (v) validate a health pass (that is, confirm that a health pass has a valid status and/or that it is not counterfeited or replayed); and (vi) decline any attempt to use a health pass in any other context (e.g., such as in a financial transaction).

In some embodiments, relying parties 150 may have or have access to a health pass validator 152 which is a set of components that may include a software application that uses a QR code or NFC interface to read a health pass token (or PAN information associated with a physical health pass) as well as test data and/or the health pass holder's picture (or the URL to that picture) as well as a server component that formats an authorization request message to be transmitted to the pass network operator 112. In some embodiments, a relying party 150 may have the ability to configure the validator 152 with specific requirements about the health pass. For example, the validator 152 may be configured to require that a test date be within a certain range (e.g., within the last 14 days) or that a certain type of test is required. Other features may be configurable to allow relying parties 150 to configure the validator 152 as needed. In some embodiments, the health pass validator 152 may further be configured to: (i) retrieve the content of a digital health pass via QR code or NFC interface (where the content may include a token, a cryptogram and additional data such as test data and information associated with the health pass holder's picture or URL to that picture and a card key); (ii) retrieve the content of a physical health pass via NFC interface (where the content includes a PAN, cryptogram, and additional data such as test data and citizen's picture or URL to that picture and a card key); (iii) retrieve the encoded citizen picture from the URL retrieved from the health pass (if such URL is provided) and decode it with the device or card key; (iv) connect to the health pass validator server/backend service, to pass card and crypto information, and receive validation from the health pass network operator 112 that the health pass is valid (not counterfeited or replayed); (v) optionally validate health pass attributes (e.g. test data) retrieved via QR code or NFC from the health pass against relying party 150 requirements; (vi) display the response (e.g. Green/Red or pass/fail, etc.) and the health pass holder's picture on the validator's screen (or on a screen associated with a point of interaction 140), or an appropriate error code if the pass is not valid.

In some embodiments, the pass validator 152 may include (or be in communication with) a validator server or backend services which: (i) formats the PAN and cryptogram information received from the health pass application into an authorization request; (ii) sends the authorization request to the pass network operator 112; (iii) receives an authorization response message from the pass network operator 112 and presents the results of the authorization response into a message for use by the pass validator 152 (e.g., to display an approval or decline with a reason code).

Referring again to FIG. 6, a brief overview of a transaction flow will now be provided by referring to the numbered messages (shown as messages "1" through "9" of FIG. 6). Again, the flow depicted in FIG. 6 is a flow in which the ID&V of a user is performed by a medical facility 166. The processing begins at "1" where the individual (operating a mobile device 130) downloads the health pass application provided by the health pass manager 108 (via the application manager 162) and sets up the application with their profile information. Processing continues at "2" where the health pass application on the mobile device 130 shares a unique application ID with the health pass manager 108 (e.g., via the issuance service provider 164).

Processing continues at "3" where the individual goes to an approved medical facility 166 to perform testing or some other health related procedure that the individual wants proof of (such as, for example, COVID-19 testing). A medical facility employee uses an enrollment application 168 to scan a QR code displayed on a screen of the individual's mobile device 130 (and generated by the health pass application installed thereon) and uses information from the QR code to retrieve information associated with the individual's identity, which the employee then validates against a government-approved ID document (e.g., such as a passport or the like). The medical facility employee interacts with the enrollment application 168 and confirms the testing or lab results of the individual. If the individual requests that a physical pass be issued, the medical facility employee provides a physical pass to the individual (or requests that such pass be sent to the individual by mail). In some embodiments, the QR code displayed on the mobile device 130 may include identity information (e.g. first name, last name picture) and an application ID (unique to the instance of the health pass application installed on the citizen's device). The QR code links the identifier to the test performed by the individual. When test results are available (could be a few days later), the lab employee enters the identifier in the enrollment application 168, along with the test results (test type and test date).

Processing continues at "4" where the enrollment application 168 transmits information to the orchestration service 172 confirming that ID&V was performed. The enrollment application 168 also transmits information associated with the lab results in an encrypted format (e.g., using a key shared by the enrollment application 168 and the orchestration service 172). At "5", the orchestration service 172 requests that the issuance service provider 164 of the health pass manager 108 issue a digital health pass to the individual. If a physical pass was already provided (or requested), the issuance service provider 164 connects to the decision management service 174 and provides the decision management service 174 with information identifying the physical pass (e.g., such as a PAN or other card identifier) and with a request to activate the physical pass.

Processing continues at "6" where the issuance service provider 164 of the health pass manager 108 requests a digital pass from the tokenization service (shown as the digital enablement service 170). In some embodiments, the digital enablement service 170 may be the tokenization service operated by Mastercard international and known as the Mastercard Digital Enablement Service (MDES) (although those skilled in the art will appreciate that other tokenization services may be used). The digital enablement service 170 issues a token (the "health pass") and associated keys and returns them to the issuance service provider 164. At "7" the issuance service provider 164 securely provisions the health pass and keys in the health pass application associated with the individual (and installed on the mobile device 130). The test results from the medical facility 166 are also securely provisioned in the health pass profile associated with the individual.

The individual is now a health pass holder, and the health pass is provisioned in association with the health pass application installed on the mobile device 130. The health pass holder may now interact with relying parties 150 to present the health pass to the relying party 150 to prove the holder's health status. For example, at "8", the health pass holder may interact with a point of interaction 140 associated with a relying party 150. The point of interaction 140 may be, for example, a scanner at an airport check in counter or the like. The scanner may operate health pass validation software as described above and may prompt the health pass holder to scan a QR code or use contactless communication to pass health pass information from the health pass application of the mobile device 130 to a pass validator 152.

Processing continues at "9" where the pass validator 152 connects to the pass network operator 112 and interacts with the network operator to confirm the validity of the health pass and to validate the test data received from the health pass application of the mobile device 130. In some embodiments, the pass validator 152 may obtain and decode a photo of the health pass holder and display it on the screen for an employee to validate. In this manner, embodiments allow secure validation of an individual's health status based on an ID&V process performed at a medical facility 166.

In some embodiments, the ID&V process may also or instead be performed remotely. Reference is now made to FIG. 7, where a system 700 is shown which is substantially similar to the system 600 of FIG. 6 with a few modifications. For example, in system 700, the identity verifier 178 performs ID&V remotely (by interacting with one or more remote identity verifiers 178 instead of performing the verification locally using an enrollment application 168 as shown in FIG. 6). The processing flow of FIG. 7 is slightly different as a result and will now be described by reference to the messages labeled "1" through "10".

At "1", an individual who wishes to obtain a health pass associated with a health status visits an approved medical facility 166 to perform testing (e.g., such as COVID-19 testing) or obtain a vaccination (such as a COVID-19 vaccination) or some other procedure. An employee or agent of the medical facility 166 registers the individual and the lab or procedure results in the medical facility 166 health record database. At "2" (which may occur before, after or at the same time as "1") the individual downloads the health pass application onto a mobile device 130. The individual may obtain the health pass application from the health pass manager 108 via an application manager 162 (which may interact with an application store such as the Google Play store or Apple App Store. Processing continues at "3" where the individual launches the health pass application, and the health pass application shares a unique application ID with health pass manager 108 via the issuance service provider 164. At "4", the individual is prompted to interact with the health pass application on the mobile device 130 to register identity information and test information into the application. The test information may be associated with an identifier or other information provided by the medical facility 166 which uniquely identifies the test results. The issuance service provider 164 transmits information to the orchestration service 172 indicating that the individual is making a claim on identity and testing results. At "5" the orchestration service 172 (or an associated ID platform) connects to one or more identity verifiers 178 and medical facilities 166 (acting as health record verifiers) to validate the individual's identity and to confirm the lab results (or to retrieve the lab results). The medical facilities 166 and the lab results may be obtained using information provided by the individual during registration.

Processing continues at "6" where the orchestration service 172 requests that the issuance service provider 164 of the health pass manager 108 issue a digital health pass and/or a physical health pass—directly or via the application manager 162. If a physical health pass is requested, a contactless card is activated when the health pass holder goes through the activation process. Processing continues at "8" where the issuance service provider 164 of the health pass manager 108 requests a digital pass from the digital enablement service 170 (which may be, for example, the Mastercard MDES tokenization service or other suitable tokenization service). The digital enablement service 170 issues a token (a health pass) and associated keys, which are then securely provisioned in the health pass application of the mobile device 130 associated with the health pass holder. The test results are securely provisioned in the health pass profile.

The individual is now a health pass holder, and the health pass is provisioned in association with the health pass application installed on the mobile device 130. The health pass holder may now interact with relying parties 150 to present the health pass to the relying party 150 to prove the holder's health status. For example, at "9", the health pass holder may interact with a point of interaction 140 associated with a relying party 150. The point of interaction 140 may be, for example, a scanner at an airport check in counter or the like. The scanner may operate health pass validation software as described above and may prompt the health pass holder to scan a QR code or use contactless communication to pass health pass information from the health pass application of the mobile device 130 to a pass validator 152.

Processing continues at "10" where the pass validator 152 connects to the pass network operator 112 and interacts with the network operator to confirm the validity of the health pass and to validate the test data received from the health pass application of the mobile device 130. In some embodiments, the pass validator 152 may obtain and decode a photo of the health pass holder and display it on the screen for an employee to validate. In this manner, embodiments allow secure validation of an individual's health status based on an ID&V process performed remotely by one or more identity verifiers 178.

The health pass manager 108 and other devices described herein might be, for example, associated with a Personal Computer ("PC"), laptop computer, smartphone, an enterprise server, a server farm, and/or a database or similar storage devices. Some or all of the processing described herein may be performed automatically or otherwise be automated by one or more computing devices or systems. For example, according to some embodiments, a health pass may be issued automatically upon matching of certain predetermined conditions (including the receipt of health pass registration data 110 as comparison of that data to one or more rules regarding issuance of a health pass). As used herein, the term "automate" may refer to, for example, actions that can be performed with little (or no) intervention by a human.

As used herein, devices described herein may exchange information via any communication network which may be one or more of a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

Figure 8:
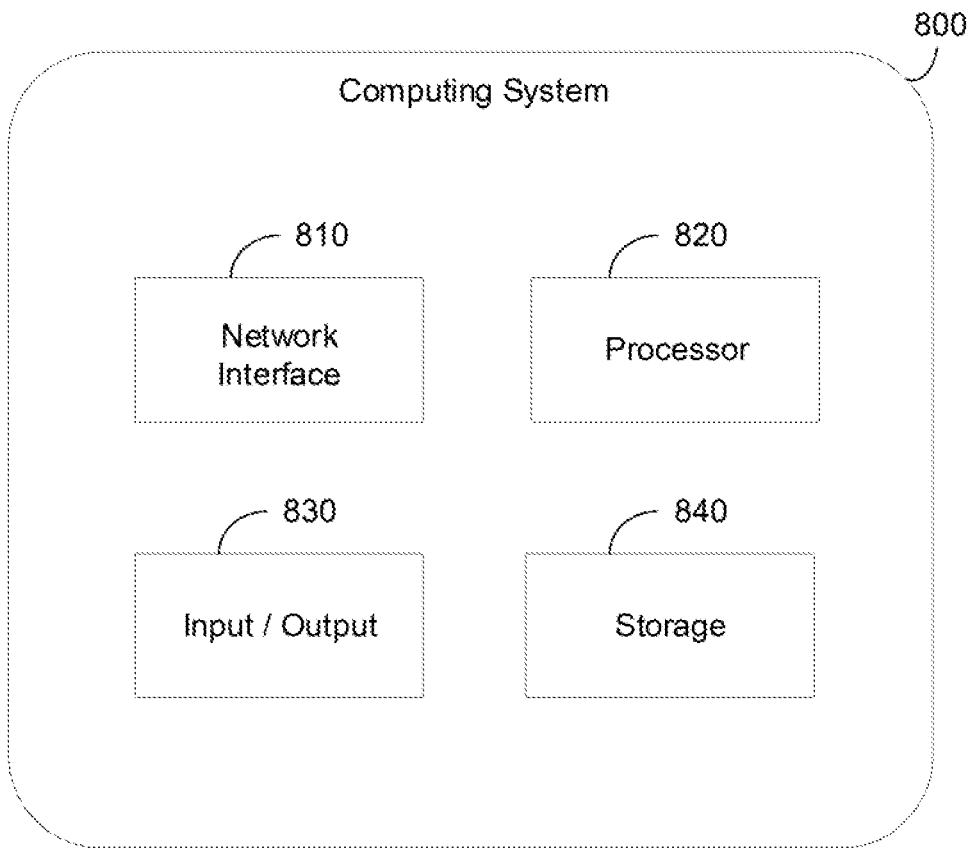
FIG. 8 is a block diagram of an apparatus in accordance with some embodiments of the present invention.

The embodiments described herein may be implemented using any number of different hardware configurations. FIG. 8 illustrates a computing system 800 that may be used in any of the methods and processes described herein, in accordance with an example embodiment. For example, the computing system 800 may be a database node, a server, a cloud platform, or the like. In some embodiments, the computing system 800 may be distributed across multiple computing devices such as multiple database nodes. Referring to FIG. 8, the computing system 800 includes a network interface 810, a processor 820, an input/output 830, and a storage device 840 such as an in-memory storage, and the like. Although not shown in FIG. 8, the computing system 800 may also include or be electronically connected to other components such as a microphone, a display, an input unit(s), a receiver, a transmitter, a persistent disk, and the like. The processor 820 may control the other components of the computing system 800.

The network interface 810 may transmit and receive data over a network such as the Internet, a private network, a public network, an enterprise network, and the like. The network interface 810 may be a wireless interface, a wired interface, or a combination thereof. The processor 820 may include one or more processing devices each including one or more processing cores. In some examples, the processor 820 is a multicore processor or a plurality of multicore processors. Also, the processor 820 may be fixed or it may be reconfigurable. The input/output 830 may include an interface, a port, a cable, a bus, a board, a wire, and the like, for inputting and outputting data to and from the computing system 800. For example, data may be output to an embedded display of the computing system 800, an externally connected display, a display connected to the cloud, another device, and the like. The network interface 810, the input/output 830, the storage 840, or a combination thereof, may interact with applications executing on other devices.

The storage device 840 is not limited to a particular storage device and may include any known memory device such as RAM, ROM, hard disk, and the like, and may or may not be included within a database system, a cloud environment, a web server, or the like. The storage 840 may store software modules or other instructions which can be executed by the processor 820 to perform any of the methods described herein. In various examples, the storage 840 may include a data store having a plurality of tables, partitions and sub-partitions. The storage 840 may be used to store database records, items, entries, and the like. Also, the storage 840 may be queried using structured or unstructured query commands (e.g., such as SQL or no SQL queries).

As will be appreciated based on the foregoing specification, the above-described examples of the disclosure may be implemented using computer programming or engineering techniques including computer software, firmware, hardware or any combination or subset thereof. Any such resulting program, having computer-readable code, may be embodied or provided within one or more non-transitory computer-readable media, thereby making a computer program product, i.e., an article of manufacture, according to the discussed examples of the disclosure. For example, the non-transitory computer-readable media may be, but is not limited to, a fixed drive, diskette, optical disk, magnetic tape, flash memory, external drive, semiconductor memory such as read-only memory (ROM), random-access memory (RAM), and/or any other non-transitory transmitting and/or receiving medium such as the Internet, cloud storage, the Internet of Things (IoT), or other communication network or link. The article of manufacture containing the computer code may be made and/or used by executing the code directly from one medium, by copying the code from one medium to another medium, or by transmitting the code over a network.

The computer programs (also referred to as programs, software, software applications, "apps", or code) may include machine instructions for a programmable processor and may be implemented in a high-level procedural and/or object-oriented programming language, and/or in assembly/machine language. As used herein, the terms "machine-readable medium" and "computer-readable medium" refer to any computer program product, apparatus, cloud storage, internet of things, and/or device (e.g., magnetic discs, opti-cal disks, memory, programmable logic devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal that may be used to provide machine instructions and/or any other kind of data to a programmable processor.

The above descriptions and illustrations of processes herein should not be considered to imply a fixed order for performing the process steps. Rather, the process steps may be performed in any order that is practicable, including simultaneous performance of at least some steps. Although the disclosure has been described in connection with specific examples, it should be understood that various changes, substitutions, and alterations apparent to those skilled in the art can be made to the disclosed embodiments without departing from the spirit and scope of the disclosure as set forth in the appended claims.

What is claimed is:

1. A computerized method, comprising:

receiving, at a network operator device, an authorization request message to identify a health status of an individual, the authorization request message transmitted from a point of interaction device and including information read from a health pass device associated with the individual, the information including: (i) an account number associated with a health pass of the individual and (ii) a cryptogram, the cryptogram generated by performing a cryptographic process on the health pass device using a secret key and the account number, wherein the authorization request message is received by the network operator device from the point of interaction device over a bankcard network;

comparing, by the network operator device, the cryptogram read from the health pass device and received in the authorization request message with information from the network operator device to authenticate the validity of the health pass by generating a second cryptogram using a network operator version of the secret key and the account number;

analyzing the cryptogram generated by the health pass device and the second cryptogram to determine if the information read from the health pass device matches the second cryptogram;

determining that the authorization request message is declined when the analysis determines that the information read from the health pass device does not match the second cryptogram;

determining that the authorization request message is approved when the analysis determines that the information read from the health pass device matches the second cryptogram;

operating the network operator device to perform a lookup of a secure database using the account number to retrieve a health status record associated with the account number in the case where the authorization request message is approved; and transmitting, in the case where the authorization request message is approved, the health status record to the point of interaction device over the bankcard network such that the health pass device does not store the health status record.

2. The computerized method of claim 1, wherein the point of interaction device is a contactless reader having a display, and further comprising displaying the health status information on the display.

3. The computerized method of claim 1, wherein the health pass device is a device associated with the individual.

4. The computerized method of claim 1, further comprising:

comparing the health status record to at least a first rule associated with the point of interaction device to cause a message to be displayed at the point of interaction device.

5. The computerized method of claim 1, wherein the authorization request message further includes information specifying one or more health pass requirements.

6. The computerized method of claim 5, wherein the health pass requirements include at least one of (i) a date or recency of a test, (ii) a type of a test, and (iii) a test vendor qualification.

7. The computerized method of claim 5, further comprising:

determining whether the health status record satisfies the one or more health pass requirements.

8. The computerized method of claim 1, wherein the health pass device is one of: (i) a mobile phone, (ii) a wearable device, and (iii) a physical chip card.

9. The computerized method of claim 1, wherein the authorization request message includes an expiry date.

10. The computerized method of claim 9, wherein the account number, the expiry date, and cryptographic data to generate the cryptogram are stored in a memory of the health pass device.

11. The computerized method of claim 1, wherein the authorization request message received from the point of interaction device is formatted as a financial transaction authorization request message and the health status record transmitted to the point of interaction device is formatted as a financial transaction authorization response message.

12. The computerized method of claim 1, further comprising:

transmitting a decline message to the point of interaction device over the bankcard network in the case where the authorization request message is declined.

* * * * *